United States Patent [19]

Brown et al.

[11] 4,177,812

[45] Dec. 11, 1979

[54] TAPE STRUCTURE AND GARMENT CLOSURE MADE THEREWITH

[75] Inventors: Robert C. Brown, Falcon Heights, Minn.; Lyle H. Mickschl, Hudson, Wis.

[73] Assignee: Minnesota Mining and Manufacturing Company, St. Paul, Minn.

[21] Appl. No.: 389,877

[22] Filed: Aug. 20, 1973

[51] Int. Cl.² .............................................. A61F 13/16
[52] U.S. Cl. ............................. 128/284; 128/DIG. 30
[58] Field of Search ............................ 2/114, DIG. 7; 117/76 A, 122 P, 122 PF; 161/102, 167, 406, 146, 147; 206/DIG. 18, 58, 411; 128/156, 284–287

[56] References Cited

U.S. PATENT DOCUMENTS

| | | | |
|---|---|---|---|
| 1,619,081 | 3/1927 | McLaurin | 156/289 X |
| 1,707,515 | 4/1929 | Evans | 161/147 X |
| 2,049,030 | 7/1936 | Strauss | 206/57 |
| 2,142,194 | 1/1939 | Karfiol | 206/56 |
| 2,532,011 | 11/1950 | Dahlquist et al. | 161/406 X |
| 2,711,739 | 6/1955 | Fishbein | 117/122 P |
| 2,755,800 | 7/1956 | Thompson | 128/156 |
| 2,829,073 | 4/1958 | Williams | 161/406 X |
| 2,931,747 | 4/1960 | Dexter | 161/406 X |
| 2,940,884 | 6/1960 | White | 161/406 X |
| 3,028,280 | 4/1962 | Hoffman | 161/406 X |
| 3,154,789 | 11/1964 | Lewis, Jr. | 2/114 X |
| 3,180,335 | 4/1965 | Duncan et al. | 128/287 |
| 3,185,394 | 5/1965 | Farrell | 128/156 X |
| 3,315,677 | 4/1967 | Tyrrel, Jr. | 161/406 X |
| 3,399,406 | 9/1968 | Bradley | 2/114 |
| 3,630,201 | 12/1971 | Endres | 128/287 |
| 3,646,937 | 3/1972 | Gellert | 128/287 |
| 3,776,234 | 12/1973 | Hoey | 128/287 |
| 3,862,634 | 1/1975 | Small | 128/284 |
| 3,874,386 | 4/1975 | Kozak | 128/287 |

Primary Examiner—Robert W. Michell
Assistant Examiner—C. F. Rosenbaum
Attorney, Agent, or Firm—Cruzan Alexander; Donald M. Sell; Richard E. Brink

[57] ABSTRACT

Pressure-sensitive adhesive tape closures for diapers or other garments are formed from backing strips which are divided into three portions of roughly equal area. One end portion and one of the other portions are surfaced with pressure-sensitive adhesive, while the remaining portion is surfaced with a release material; the latter two portions are folded together. In use, the first end portion is adhered to one garment border, a second border juxtaposed or overlapped, the folded portion of the closure then unfolded, and the thus-exposed adhesive surface adhered to the second border. These closures may be formed by cutting parallel strips across an elongate sheet of appropriately configured convolutely wound adhesive-coated sheet material.

5 Claims, 11 Drawing Figures

TAPE STRUCTURE AND GARMENT CLOSURE MADE THEREWITH

BACKGROUND OF THE INVENTION

This invention relates to pressure-sensitive adhesive sheet material, to garment closures made therefrom, and to garments incorporating such closures.

In the past, a wide variety of devices have been used for closing garments, e.g., hooks and eyes, buttons, snaps, zippers, hook-and-loop fasteners, buckles, etc. Each of these devices is useful in appropriate circumstances, but each requires expensive findings, separate operations for attaching the two cooperative parts of the closure, or both. Safety pins are commonly employed in fastening a garment such as a diaper, but they are often inconvenient to apply and are prone to come open and injure the wearer of the garment.

Strips of normally tacky and pressure-sensitive adhesive tape have also been used as means of closure; see, e.g., U.S. Pat. Nos. 3,180,335, 3,630,201, and 3,646,937. The use of pressure-sensitive adhesive tape strips is particularly appealing for "throwaway" items such as nonwoven medical examination robes, temporary lab smocks, disposable diapers, and the like. Such strips, however, must be either cut from a roll at the time of use, provided with a readily removable liner, or both. The first of these techniques is inconvenient and the second involves a liner disposal problem.

The aforementioned U.S. Pat. No. 3,646,937 states that a linered tape strip which protrudes beyond the edge of a diaper prior to use results in inconvenient handling; if the liner inadvertently becomes detached, it may be ingested by the baby, and the adhesive itself may stick to some undesired location. To cope with these problems, the patentee coats pressure-sensitive adhesive on the back of the release liner, thus permanently adhering it to the underside of the diaper border. A pressure-sensitive adhesive strip is then so positioned that one end portion adheres to the upper side of the diaper border, with the remainder of the strip bending around the edge and contacting the release liner. At the time of use, the lower portion of the strip is pulled free from the liner and adhered to the desired location on a juxtaposed or overlapped border of the garment. To prevent the portion of the strip in contact with the liner from pulling free at an inopportune time, a small area of the liner may be modified to provide increased adhesion.

Although the diaper closure just described is not only mechanically effective but also commercially successful, certain problems are associated with its use. For example, it requires the separate application of adhesive to the garment-contacting portion of the liner. Where the closure is used to hold disposable diapers on an active baby, the pressure-sensitive adhesive may span the gap between adjacent borders of a diaper, come in contact with the baby's tender skin and cause irritation.

In summary, tape closures have shown great promise for use on disposable garments, but each of the closures heretofore available has been subject to faults which limited its use.

BRIEF SUMMARY OF THE INVENTION

The invention provides a simple, inexpensive, and convenient pressure-sensitive adhesive tape closure having particular utility for use on disposable garments. The closures may be prepared in advance of the time they are needed. Neither application of a release liner to the garment nor application of adhesive to the liner back is required. In the most preferred embodiment, the possibility of having pressure-sensitive adhesive in contact with human skin is virtually eliminated.

The closures of the invention are readily formed from an elongate normally tacky and pressure-sensitive adhesive tape structure wound convolutely upon itself in roll form. This structure comprises a sheet backing which has a back side, a face side and spaced lateral edges. A strip of normally tacky and pressure-sensitive adhesive is firmly adherently bonded to the face side of the backing, at least along an area adjacent each of the lateral edges. In an area over the face side, extending along the long dimension of the structure, the structure has an exposed surface which displays release characteristics to the adhesive. As will subsequently be shown in greater detail, there are several ways in which structures of this type can be embodied.

Closure members in accordance with the invention can be formed by cutting the structure discussed in the preceding paragraph on generally parallel lines extending across its longitudinal axis. The resultant closure member then comprises a backing strip having a face side and a back side, which strip includes two end portions and an intervening central portion. The three portions have roughly the same area, the area of the central portion usually being about $\frac{1}{4}$ to $\frac{1}{2}$ of the total area of the face side. A layer of normally tacky and pressure-sensitive adhesive is firmly adherently bonded to the face side of the backing strip over one end portion and at least one of the two other portions. The uppermost surface of one of these two portions is so prepared as to exhibit release properties with respect to pressure-sensitive adhesives, and the uppermost surface of the remaining portion displays normally tacky and pressure-sensitive properties. For convenience, the closure member is folded so that the uppermost surfaces of the last two portions are disposed in face-to-face contact. The exposed end portion can then be adhered to a first border of a garment, a second border of a garment overlapped, or juxtaposed with respect to the first border, the closure member unfolded, and the exposed pressure-sensitive adhesive surface bonded to the second border, thus holding the garment in closed position.

BRIEF DESCRIPTION OF THE DRAWINGS

Understanding of the invention will be facilitated by referring to the accompanying drawings, in which like numbers refer to like parts in the several views, and in which.

DESCRIPTION OF PRESENTLY PREFERRED EMBODIMENTS

Figure 1:
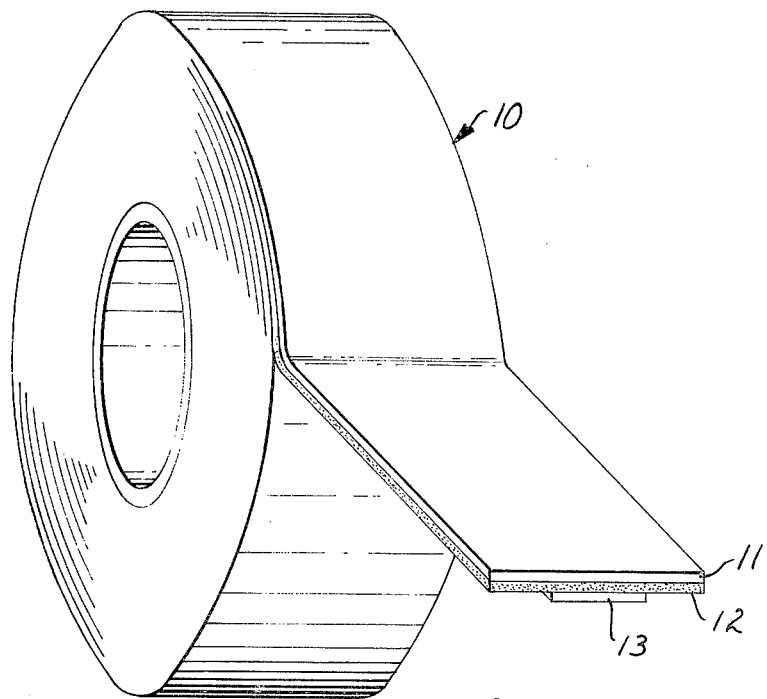
FIG. 1 is a perspective view of a roll of pressure-sensitive adhesive tape 10, in accordance with the invention, from which tape closures of the invention may be prepared.

Although the structures now to be described are subject to numerous variations without departure from the spirit of the invention, it is believed that understanding will be facilitated by a consideration of specific representative types*. All parts are by weight unless otherwise noted.

*Especially in their intermediate forms, some of the structures superficially resemble variations of the popular adhesive strip bandages; see, e.g., U.S. Pat. No. 2,755,800, which shows a strip of adhesive tape having a metal foil patch covering the central portion, for use as a pad for corns. As will be shown, however, the function and nature of the invention impose requirements clearly distinguishing over such art.

EXAMPLE 1

A pressure-sensitive adhesive tape structure of the type shown in FIG. 1 was prepared as follows:

A 5.5-mil neoprene-unified paper backing, weighing 60 pounds per papermaker's ream, was coated with a pigmented rubbery 67:33 styrene:butadiene copolymer of latex solids, and the water evaporated to leave approximately 8 lbs. of copolymer per ream. Over this coating was then applied a low adhesion release coating comprising a 5% solution of polyvinyloctadecyl carbamate in an aromatic solvent, and the solvent evaporated in an oven. The thus-treated paper weighed approximately 65-70 pounds per papermaker's ream.

A rubber-resin pressure-sensitive adhesive was prepared by milling together 100 parts crude rubber, 25 parts titanium dioxide, and 2 parts antioxidant, thereafter stirring the milled blend with 125 parts polyterpene resin into 893 parts heptane. The thus-obtained 22% solids adhesive solution was then coated on the face side of the backing and the heptane evaporated to leave a dry adhesive weight of 10 grains per 24 square inches. The adhesive-coated backing was then wound convolutely about a core to form a roll, slit to 3-inch widths, each of which was then again wound in roll form.

A ½-mil biaxially oriented polyethylene terephthalate film was corona-treated and then coated with a 2% heptane-xylene-methylethyl ketone solution of polydimethyl siloxane (e.g., "Syloff" 2330, available from Dow-Corning Company with fast cure additives), the solvent evaporated, and the coated film wound convolutely about a core to form a roll. The coated film was then slit to ⅜-inch width, the central portion being exposed to a corona discharge treatment along a narrow path to locally decrease the release characteristics of the silicone resin. (The same effect can be obtained, of course, by merely omitting application of the silicone release coating to a narrow strip extending along the same, removing a strip of the silicone by abrasion, punching one or more holes in the silicone coated portion of the backing, etc.)

The thus-treated release-coated ⅜-inch wide polyester film was then laminated approximately centrally on the pressure-sensitive adhesive-coated surface of the 3-inch wide paper backing and the resultant product wound convolutely in roll form. A structure 10 of this general type is shown in FIG. 1 of the drawing, in which backing 11 is coated with pressure-sensitive adhesive layer 12 and release strip 13 located centrally thereof.

Figure 2:
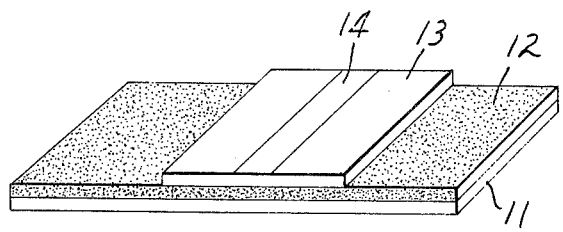
FIG. 2 is a perspective view of a tape closure in accordance with the invention, conveniently made by cutting a strip across the end of the tape structure of FIG. 1.
Figure 3:
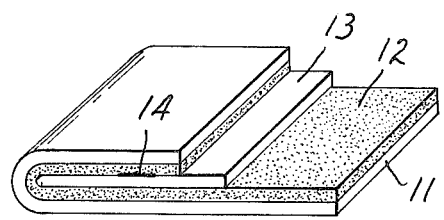
FIG. 3 is a perspective view showing the closure of FIG. 2 in folded form.

To form garment closures in accordance with the invention, the tape structure of FIG. 1 is severed at right angles to the lateral edges to form intermediate products of the type shown in FIG. 2, which indicates the narrow band 14 in which release liner 13 has been treated to locally increase affinity for pressure-sensitive adhesives. FIG. 3 shows a closure member formed from the intermediate product of FIG. 2, the left end of the closure strip having been folded over the release liner 13 so that the pressure-sensitive adhesive surface 12 comes in contact with the release surface of the liner 13.

Figure 8:
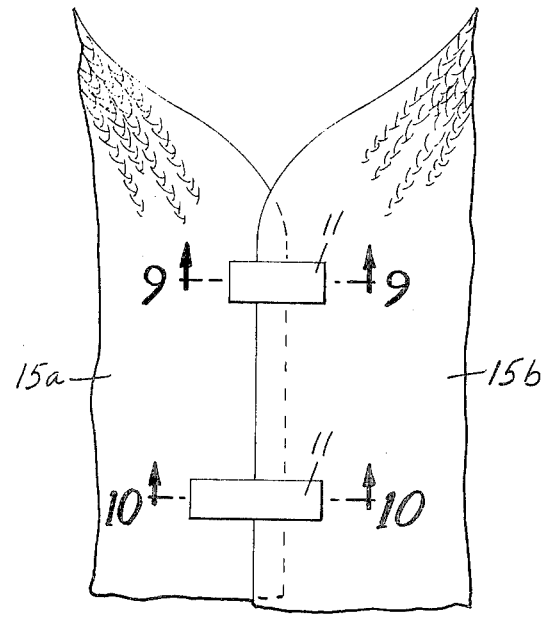
FIG. 8 is a plan view showing two closures of the type depicted in FIG. 2 and 3 applied to a garment, the upper closure being applied to only one garment border and the lower closure spanning two overlapped garment borders.
Figure 9:
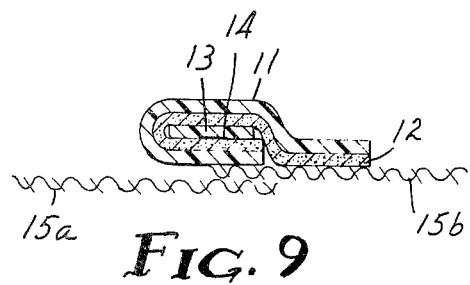
FIG. 9 is a cross-sectional view of the upper closure in FIG. 8, looking in the direction of the arrows.
Figure 10:
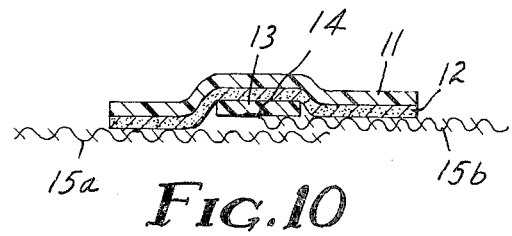
FIG. 10 is a cross-sectional view of the lower closure in FIG. 8, looking in the direction of the arrows.

FIGS. 8-10 inclusive demonstrates the way in which the closure member of FIG. 3 is used on a diaper or other garment which is to be held in predetermined closed position. The right end portion of the closure is adhered to garment border 15b, the remainder of the closure being kept folded until such time it is to be used. In this preliminary position, the folded edge of the closure extends slightly beyond the edge of garment border 15b; when the closure is to be attached, the user places garment border 15a in either adjacent or overlapping position with respect to garment border 15b, grasps the folded portion of the closure in one hand, and bends it upward. This action frees the previously folded end of the closure, lifting the end portion of the pressure-sensitive adhesive coating 12 free from the release surface, so that it can be grasped and then adhered in position on border 15a. FIG. 10 shows an arrangement in which the exposed release surface of liner 13 will span any slight gap which may exist between the adjacent edges of garment borders 15a and 15b, thereby protecting any underlying surface (especially, in the case of diapers, a baby's tender skin) from contact with the pressure-sensitive adhesive.

Figure 11:
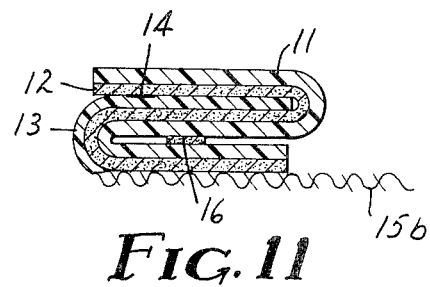
FIG. 11 is a cross-sectional view of a closure similar to the upper closure in FIG. 8 but mounted on the garment border in a different manner.

As previously noted, in some instances it is desirable to avoid having a closure tab extend beyond the edge of a garment. The embodiment of the invention depicted in cross-sectional view in FIG. 11 incorporates a convenient means of achieving this objective. Basically, this embodiment is quite similar to that of FIG. 8, except that the folded end of the closure is doubled over the exposed back side of backing 11, thus imparting a generally Z-shaped cross-sectional appearance. To prevent the closure from prematurely unfolding, a small (e.g., ⅛ inch diameter) spot of hot melt or other suitable adhesive 16 may be interposed between the adjacent surfaces of backing 11 to lightly bond them together. This light bonding is easily broken, at the time the closure is to be used for its intended purpose, by merely peeling apart the juxtaposed surfaces of backing 11. A suitable hot melt adhesive is available from Eastman Chemicals as "Eastobond" L-8080-293C.

EXAMPLE 2

The general construction and manufacturing procedure for the product of this example are the same as in Example 1, with the following exceptions: (1) the treated paper backing is replaced with 1.5-mil biaxially oriented polyethylene terephthalate film; (2) the pressure-sensitive adhesive is a 95.5:4.5 iso-octylacrylate:acrylic acid copolymer of the type disclosed in U.S. Pat. No. Re. 24,906; and (3) the film used for the release liner is white-pigmented 2.5-mil linear polyethylene.

EXAMPLE 3

A biaxially oriented polyethylene terephthalate film backing of the type described in Example 2 is coated with 2-inch wide stripes of the acrylate pressure-sensitive adhesive referred to in Example 2, spaced one inch apart and extending along the entire length of the film. After partially evaporating the solvent from the pressure-sensitive adhesive, the uncoated 1-inch wide exposed face of the backing film is coated with a toluene solution of polyvinyl octadecyl carbamate release agent, described in U.S. Pat. No. 2,532,011, and the coated film is then subjected to further heating to complete removal of the solvent. The resultant structure is slit along the middle of each 2-inch wide pressure-sensitive adhesive strip and each individual section wound about a core in roll form. In use, a 1-inch strip of the structure is cut from the end, resulting in a 1-inch×3-inch product having pressure-sensitive adhesive portions adjacent each end, with a release-coated portion between the adhesive portions; this intermediate product is then converted to a closure member by folding one adhesive-coated end portion over and into contact with the release-coated portion. The release agent employed displaying a greater affinity for pressure-sensitive adhesive than the silicone resin of Examples 1 and 2, no additional adhesionincreasing treatment is necessary. This form of the product avoids the use of unnecessary quantities of pressure-sensitive adhesive, reduces cost by elimination of a separate release liner, and results in a thinner closure member than that of FIG. 3.

EXAMPLE 4

Figure 6:
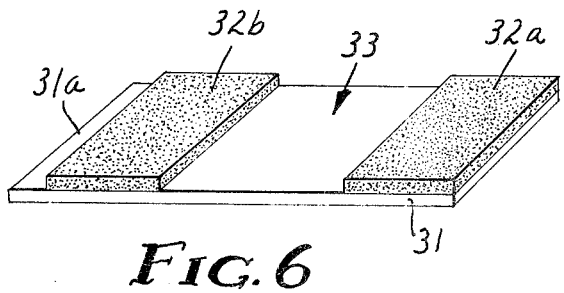
FIG. 6 is a perspective view analogous to that of FIG. 2, but depicting another embodiment of the invention.
Figure 7:
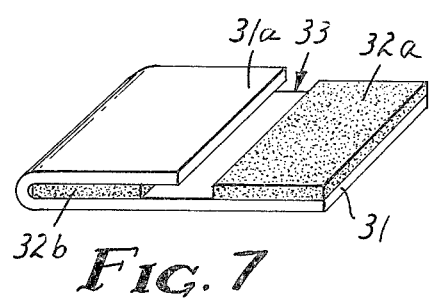
FIG. 7 is a perspective view showing the closure of FIG. 6 in folded form.

The components and manufacturing procedure for the closure member of this example are substantially the same as in Example 3 except that the widths of the various stripes on the face side repeat the following sequence: (1) pressure-sensitive adhesive, 2-inch; (2) release coating, ¾-inch; (3) pressure-sensitive adhesive, 1-inch; (4) uncoated, ¼-inch, (5) pressure-sensitive adhesive, 1-inch; (6) release coating, ¾-inch, (7) pressure-sensitive adhesive, 2-inch. The structure is converted into 3-inch wide lengths by slitting down the middle of stripes 1 and 4. When 1-inch strips are cut from the end of such a 3-inch roll, intermediate products like that of FIG. 6 result. The face of backing 31 is provided with pressure-sensitive adhesive portions 32a and 32b adjacent the opposite ends, center portion 33 remaining uncoated; pressure-sensitive portion 32b does not, however, extend completely to the end of the strip, leaving ¼-inch×1-inch tab 31a uncoated. When the intermediate structure is folded to form a closure member, as shown in FIG. 7, tab 31a becomes available to aid in unfolding the folded end.

EXAMPLE 5

Figure 4:
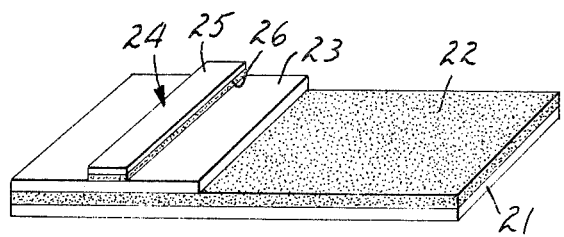
FIG. 4 is a perspective view to FIG. 2 but showing another embodiment of the invention.
Figure 5:
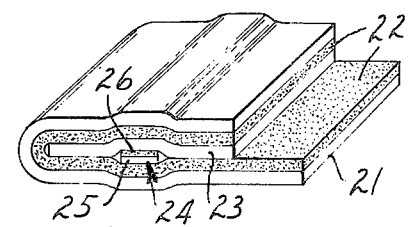
FIG. 5 is a perspective view showing the closure of FIG. 4 in folded form.

The same general manufacturing procedure described in Examples 1 or 2 is followed, produding tape closures of the type shown in FIGS. 4 and 5. Backing 21 is coated on its face side with a layer of normally tacky and pressure-sensitive adhesive 22, release strip 23 being applied along one edge. Overlying release strip 23 is a thin strip of tape 24, comprising a backing 25 coated with a layer of pressure-sensitive adhesive 26 which has excellent affinity for silicone release surfaces. The exposed back side of backing is of a type to which conventional pressure-sensitive adhesive adheres far more tenaciously than it does to a silicone surface. A suitable tape 24, having a 1-mil transparent-biaxially oriented polyethylene terephthalate and a silicone-based pressure-sensitive adhesive, is available from Minnesota Mining and Manufacturing Company under the registered trademark "SCOTCH" Brand Pressure-Sensitive Adhesive Tape Y-9030.

As has previously been indicated, the foregoing examples are for illustrative purposes only, and many variations will occur to those ordinarily skilled in the art. For example, even where a silicone release coating is employed, it is not always necessary or desirable to locally modify a portion of the surface to increase its receptivity to pressure-sensitive adhesives. As is particularly shown in FIG. 9, inadvertent or premature unfolding of the folded part of the closure is inhibited by the pressure of garment border 15b. Where, however, it is desired to increase adhesion locally, any of the techniques disclosed in U.S. Pat. No. 3,646,937 (the disclosure of which is incorporated herein by reference) may be used. It will likewise be recognized that the various shapes, dimensions, adhesives, backings and coatings are intended to be typical but not to restrict the scope of the invention. Accordingly, the invention is defined only by the appended claims, which should be considered with full regard to the doctrine of equivalents.

I claim:

1. In a disposable diaper having a top sheet, a backing sheet and an absorbent core interposed therebetween, a means for providing self-stored protective access to a portion of the adhesive surface of a diaper tape fastener comprising, a pressure-sensitive tape fastener having an upper surface and a lower surface, said lower surface being divided widthwise into two end segments at least one of which is adhesively treated and a middle segment containing a release agent, one of said segments being a fixed end segment which is secured to said backsheet, the other of said end segments being a releasable end segment; said fastener being folded in manner such that said releasable end segment and said middle segment are superimposed over said fixed end segment with the lower surface of said releasable end segment being in contacting relation and releasably secured to the lower surface of said middle segment.

2. A disposable diaper as claimed in claim 1 wherein the contacting lower surfaces of the middle segment and the releasable end segment are bonded together with a small spot of hot melt adhesive.

3. A disposable diaper as claimed in claim 1 wherein said fixed end segment is secured to said backing sheet by adhering said fixed end segment to said backing sheet.

4. A disposable diaper as claimed in claim 1 wherein said release agent on said middle segment is silicone.

5. A disposable diaper as claimed in claim 1 wherein said releasable end segment has an end portion on the lower surface of said pressure-sensitive tape fastener which is not treated with adhesive.

* * * * *

UNITED STATES PATENT AND TRADEMARK OFFICE
CERTIFICATE OF CORRECTION

PATENT NO. : 4,177,812

DATED : December 11, 1979

INVENTOR(S) : Robert C. Brown

It is certified that error appears in the above–identified patent and that said Letters Patent are hereby corrected as shown below:

Lyle H. Mickschl should be removed as one of the inventors.

Col. 5, line 32, "adhesionincreasing" should read --adhesion-increasing--.

Signed and Sealed this

First Day of April 1980

[SEAL]

Attest:

SIDNEY A. DIAMOND

Attesting Officer

Commissioner of Patents and Trademarks